United States Patent [19]
Pedersen et al.

[11] Patent Number: 5,356,437
[45] Date of Patent: Oct. 18, 1994

[54] REMOVAL OF EXCESS DYE FROM NEW TEXTILES

[75] Inventors: Gitte Pedersen, Frederiksberg C, Denmark; Michael Schmidt, Gau-Köngernheim, Fed. Rep. of Germany

[73] Assignee: Novo Nordisk A/S, Bagsvaerd, Denmark

[21] Appl. No.: 129,185

[22] PCT Filed: Apr. 10, 1992

[86] PCT No.: PCT/DK92/00118
§ 371 Date: Oct. 7, 1993
§ 102(e) Date: Nov. 9, 1993

[87] PCT Pub. No.: WO92/18687
PCT Pub. Date: Oct. 29, 1992

[30] Foreign Application Priority Data

Apr. 12, 1991 [EP] European Pat. Off. ........ 91610032.4

[51] Int. Cl.$^5$ ................. C11D 3/395; C11D 3/39
[52] U.S. Cl. ........................ 8/401; 252/174.12
[58] Field of Search ................. 8/401, 549, 111; 252/174.12

[56] References Cited

U.S. PATENT DOCUMENTS 4,421,668 12/1983 Cox et al. ................. 8/111 X
5,131,918 7/1992 Kelley ..................... 8/549

FOREIGN PATENT DOCUMENTS

WO89/09813 10/1989 PCT Int'l Appl. .
WO91/05839 5/1991 PCT Int'l Appl. .
2101167 1/1983 United Kingdom .

*Primary Examiner*—Arthur C. Prescott
*Attorney, Agent, or Firm*—Steve T. Zelson; Elias J. Lambiris

[57] ABSTRACT

Dye leached from dyed or printed textiles in an aqueous solution can be decolorized by adding enzymes that utilize hydrogen peroxide or molecular oxygen for the oxidation of organic or inorganic substances, including colored substances, together with a source of $H_2O_2$ or $O_2$. Such enzymes are usually termed peroxidases and oxidases, respectively. This treatment reduces the risk of back-straining (redeposition of dye onto textile) even when less water is used. The enzymatic bleaching of released dyestuff will decrease process time as well as the amount of energy and water needed to achieve a satisfactory quality of the textile, and the color of the waste water is reduced.

15 Claims, No Drawings

REMOVAL OF EXCESS DYE FROM NEW TEXTILES

FIELD OF INVENTION

The present invention relates to removal of excess dye from newly manufactured printed or dyed fabric or yarn.

BACKGROUND OF THE INVENTION

In printing of textiles, it is common to use a printing paste containing a dye and a thickener. Among the commonly used thickeners are biological polymers and chemically modified biological polymers, such as alginate, galactomannan, starch and carboxymethyl cellulose. But also synthetic thickeners can be used.

With most printing methods, the polymer and excess dye must be removed by washing with water after the fixation of the print. Generally, a large amount of water is required for complete removal of excess dye due to the risk of back-staining during the process, i.e. redeposit on the fabric of already dissolved dye, which may cause unwanted dye transfer during laundering by the consumer. The risk of back-staining is significant in the early stages of the rinsing and/or at high temperatures, especially when the polymer is quickly solubilized.

After dyeing of fabric or yarn, the excess dyestuff, after the fixation, has to be removed by washing with water. Generally, a large amount of water is required for complete removal of excess dye, and during washing the backstaining of released dyestuff will result in an insufficient wet fastness unless the washing is repeated several times.

When garments sewn of differently dyed fabrics are subjected to a wet treatment, e.g. for desizing or so-called "stone-washing" of denim, there is a risk of dye transfer.

In a conventional process the printed or dyed textile is first rinsed with cold water, then washed at high temperature with the addition of a suitable additive to decrease backstaining like PVP. The process is repeated until satisfactory amount of dyestuff (and thickener) have been removed. A polyvinyl pyrrolidone (PVP) can be added as a retarder to reduce backstaining during hot washing, but this compound does not bleach the dye and is relatively expensive. The waste water from a conventional process tends to be strongly coloured and may represent a disposal problem.

SUMMARY OF THE INVENTION

We have developed an improved process for removal of excess dye, wherein dye leached from dyed or printed textiles is decolourized in an aqueous solution by adding enzymes that utilize hydrogen peroxide or molecular oxygen for the oxidation of organic or inorganic substances, including coloured substances, together with a source of $H_2O_2$ or $O_2$. Such enzymes are usually termed peroxidases and oxidases, respectively. This treatment reduces the risk of back-staining (redeposition of dye onto textile) even when less water is used. The enzymatic bleaching of released dyestuff will decrease process time as well as the amount of energy and water needed to achieve a satisfactory quality of the textile, and the colour of the waste water is reduced.

The process of the invention can result in a decreased number of washes, thereby increasing the productivity and decreasing the consumption of water and chemicals. It can also lead to a decreased dye-load in the waste water, thus reducing water pollution. Further, the quality of the treated textile can be increased (e.g. improved dye-fastness).

Accordingly, the present invention provides a process for removal of excess dye from newly manufactured printed or dyed fabric or yarn comprising treatment with a wash liquor containing (1) an enzyme exhibiting peroxidase activity and a suitable source of $H_2O_2$ or (2) an enzyme exhibiting a suitable oxidase activity and a source of $O_2$.

It is well recognized in the art (cf. for instance B. C. Saunders et al., *Peroxidase*, London, 1964, p. 10 ff.) that peroxidases act on various amino and phenolic compounds resulting in the production of a colour. In view of this, it must be considered surprising that peroxidases (and certain oxidases) may also exert an effect on coloured substances in solution such that backstaining is inhibited.

It has been reported that peroxidases may decolorize certain natural pigments like 3-hydroxyflavone, carotene and betalain (W. Schreiber, *Biochem. Biophys. Res. Commun.* 63 (2), 1975, pp. 509–514; A. Ben Aziz, *Phytochemistry* 10., 1971, pp. 1445–1452; B. P. Wasserman, J. Food Sci. 49, 1984, pp. 536–538). Contrary to these natural compounds, the commonly used textile dyes, when dissolved or dispersed in wash liquors, are generally resistant to oxidation by atmospheric oxygen and also, to a greater or lesser extent, to hydrogen peroxide itself.

DETAILED DISCLOSURE OF THE INVENTION

Fabric or Yarn

The process of the invention is applicable to all types of textile materials, both natural fibers (NF) and man-made fibers (MMF) as well as any combination hereof. Typical examples are cellulosic fibres (e.g. cotton and flax), cellulose fibers (e.g. acetate and triacetate), protein fibers (e.g. wool and silk), polyamide fibers (e.g. nylon 6 and 6,6), polyester fibers (e.g. polyethylene terephthalate) and acrylic fibers.

The process of the invention may be applied to dyed yarn, to knitted, woven or nonwoven fabric, or to garments made from dyed and/or printed fabric, especially garments made from differently coloured material.

Printing Method

The process of the invention is suited for excess dye bleaching after any kind of textile printing. Examples of commonly used techniques are printing on a Rotation film, a Rouleaux, a Flash film, a Transfer film device. After printing the dye is fixed on the textile by e.g. steaming or treatment with hot air.

Dyeing Method

The process of the invention is suited for excess dye bleaching after any kind of dyeing. The dyeing of textiles is generally carried out by passing the fabric through a concentrated solution of dye, followed by storage of the wet fabric in a vapour tight enclosure to permit time for diffusion and reaction of the dye with the fabric substrate prior to washing off unreacted dye. Alternatively, the dye may be fixed by subsequent steaming of the textile prior to washing. Dyeing of yarn is done in a similar manner.

Dyestuff

The process of the invention is particularly suited for bleaching of any kind of dye composing an aromatic amino group or a phenolic group or the like e.g. an azo-group or an anthraquinone; or for bleaching of dyes by the radicals formed by the action of the bleaching enzyme on another substrate. The dyes include synthetic and natural dyes. Typical dyes are those with anionic functional groups (e.g. acid dyes, direct dyes, Mordant dyes and reactive dyes), those with cationic groups (e.g. basic dyes), those requiring chemical reaction before application (e.g. vat dyes, sulphur dyes and azoic dyes), disperse dyes and solvent dyes.

A comprehensive catalogue of commonly used textile dyes, both synthetic (such as azo dyes) and natural or nature-identical (by which is meant a substance which is produced synthetically, but which in structure and properties is identical to the natural compound), e.g. indigo, is found in the *Colour Index*, 3rd ed. Vol. 1–8.

Enzyme

Examples of suitable oxidases and peroxidases are those which use molecular oxygen or hydrogen peroxide to oxidize aromatic compounds, such as phenols, polyphenols and aromatic amines. For the sake of convenience, such as oxidases and peroxidases are collectively termed bleaching enzymes in the following.

Examples of suitable bleaching enzymes are catechol oxidase (EC 1.10.3.1), laccase (EC 1.10.3.2), peroxidase (EC 1.11.1.7), chloride peroxidase (EC 1.11.1.10) and phenol oxidase (EC 1.14.18.1).

Bleaching enzymes which may be employed for the present purpose may be derived from plants (e.g. horse-radish peroxidase) or microorganisms such as fungi or bacteria. Examples of suitable peroxidases are those derived from a strain of Coprinus, e.g. *C. cinerius* or *C. macrorhizus*, or from a strain of Bacillus, e.g. *B. pumilus*, particularly peroxidase according to PCT/DK 90/00260. Such enzymes may be produced, by methods known in the art, by cultivating the strain on a suitable nutrient medium or by transferring the genetic information to a suitable host organism and cultivating this.

A suitable amount of the enzyme is generally 0.01–100 mg of enzyme protein per liter of bleach liquor, particularly 0.1–10 g/l.

Particularly preferred bleaching enzymes are those which are active at pH values of 4.5–10.5, particularly 5.5–9.5, e.g. 6.5–9.

$O_2$ or $H_2O_2$ Source

Molecular oxygen will usually be present in sufficient quantity.

Suitable sources of $H_2O_2$ are $H_2O_2$ itself, percarbonates and perborates. When the bleaching enzyme employed in the invention is a peroxidase, $H_2O_2$ may be added at the beginning or during the process, e.g. in an amount of 0.01–50 mM, particularly 0.1–5 mM. When using Coprinus peroxidase, 0.1–2 mM $H_2O_2$ is preferred, and with *B. pumilus* peroxidase 0.2-mM $H_2O_2$.

It may be desirable to utilize an enzymatic process for hydrogen peroxide formation. Thus, the wash liquor may additionally comprise an enzymatic system (i.e. an enzyme and a substrate therefor) which is capable of generating hydrogen peroxide, e.g. glucose and glucose oxidase.

Wash Liquor

It has surprisingly been found that the addition of another oxidizable substrate (for the bleaching enzyme used in the process of the invention) at the beginning or during the washing and/or rinsing process may enhance the backstaining inhibitory effect of the bleaching enzyme employed. This is thought to be ascribable to the formation of short-lived radicals or other oxidised states of this substrate which participate in the bleaching or other modification of the coloured substance. Examples of such oxidizable substrates are metal ions, e.g. $Mn_{++}$, halide ions, e.g. chloride or bromide ions, or organic compounds such as phenols, e.g. p-hydroxycinnamic acid, 2,4-dichlorophenol, p-hydroxybenzene sulphonate, vanillin, p-hydroxybenzoic acid. Other examples of phenolic compounds which may be used for the present purpose are those given in M. Kato and S. Shimizu, *Plant Cell Physiol*. 26(7), 1985, pp. 1291–1301 (cf. Table 1 in particular) or B. C. Saunders et al., op. cit., p. 141 ff. The amount of oxidizable substrate to be added is suitably between about 1 µM and 1 mM.

Process Conditions

In the case of printed textile, the process of the invention can advantageously be carried out simultaneously with the process of EP 91610022.5. In the case of denim textiles (especially indigo-dyed denim), the bleaching process according to the invention can be carried out simultaneously with a treatment with cellulase (and optionally pumice) to create a desired worn look by forming local variations in colour density, as described in American dye stuff reporter, Sept. 90, D. Kochavi, T. Videbask and D. Cedroni, Optimizing processing conditions in enzymatic stone washing. The process of the invention can also be carried out simultaneously with enzymatic desizing, i.e. removal of starch size by means of an α-amylase.

The enzyme treatment can be applied in one of the washes of the printed or dyed fabric or dyed yarn, preferably the first hot wash. The process may be run in batch mode or continuous mode. The process may be applied on a winch, a beck, a jet dyer, a open-width washing machine, a J or U-box, a steamer, or any other equipment available suitable for a washing process.

The process conditions must be chosen according to the characteristics of the enzyme in question. They are generally in the range 20°–100° C., pH 4.5–10.5, typically 30°–90° C., pH 5.5–9.5 especially 40°–75° C., pH 6.5–9.

EXAMPLE 1

Rinsing of Printed Textile

A knitted fabric printed on one side with a print paste containing sodium alginate as sole thickener and a blue reactive dye was cut into small pieces of 1.00 g.

The three pieces covered 100% with print paste, were rinsed together in excess cold water for 20 min. The pieces were added to 3 Erlenmeyer beakers respectively, containing 20 g of buffer with the following composition: 1.8 mM Citric acid, 6.4 mM orthophosphate, 60 ppm $Ca^{++}$, pH 7.0. To each beaker 5 stainless steal balls (d=0.5 cm) were added. To beaker nr 1 and 2, 2 mM hydrogen peroxide was added. To beaker nr 1, 0.4 mg of a freeze dried preparation of peroxidase from *Coprinus macrorhizus* (CMP) purchased from Chemical Dynamics Corporation (Lot no: 137 836) containing approximately 40% pure peroxidase protein judged from the theoretically RZ value.

The experiment was performed with sealed beakers in a water bath at 40° C. for 30 min with a back and forth motion of 135 motions per minute. The reaction was stopped by applying the pieces of fabric to a second cold rinse with excess water for 30 min. The optical density (OD) of the washing liquor at 570 nm was measured. The results are given in table 1.

TABLE 1

|  | $OD_{570}$ Wash no. 1 |
|---|---|
| No enzyme | 1.27 |
| +2 mM $H_2O_2$ | 1.31 |
| +20 mg/l CMP, 2 mM $H_2O_2$ | 0.19 |

The back of the print was evaluated visually after the wash. Addition of CMP did significantly decrease the amount of backstaining.

EXAMPLE 2

Bleaching of Reactive Dyes

The reactive dyes shown below were tested. Primazin and Basilin are products of BASF, Benzaktiv of CHT and Remazolturkisblau of Hoechst (all Germany). Also shown are the type of reactive group and the wave length used for following the bleaching reaction (this was chosen as the wave length with the highest reaction rate and may be slightly different from the wavelength of maximum OD).

| Reactive dyes tested | | |
|---|---|---|
| Name | Reactive group | OD at nm |
| 1 Primazin Brilliant Violet RL | Vinylsulfone | 560 |
| 2 Primazin Brilliant Blue RL | Vinylsulfone | 595 |
| 3 Primazin Brilliant Red 2B | Vinylsulfone | 510 |
| 4 Primazin Brilliant Green 6BL | Vinylsulfone | 622 |
| 5 Basilin Navy Blau E-RN | Monochlortriacin | 606 |
| 6 Basilin Scharlach E-2G | Monochlortriacin | 504 |
| 7 Benzaktiv Blau S-FR | Bifunctional | 612 |
| 8 Remazol Turkisblau | Vinylsulfone | 666 |

Bleaching experiments were performed at room temperature in a 1 ml quartz cuvette using *C. macrorhizus* peroxidase together with p-hydroxybenzene sulphonate (PSP) or vanillin (VAN) as accelerator. The reaction was initiated by the addition of hydrogen peroxide, and absorption spectra were recorded over the wave length range from 200 nm to 800 nm, once every 6 seconds for 1 minute and once every 30 seconds for 5 minutes. The bleaching rate is given as the change in optical density at the wavelength shown above. The bleaching had the following composition:

| Dye | 40 mg/l |
|---|---|
| Accelerator | 5 μM(PSP or VAN) |
| $H_2O_2$ | 0.25 mM or 2.5 mM |
| Buffer | 0.2M phosphate + 0.1M citric acid, pH 7 |

The results were as follows, given as reaction rate in absorption units per minute:

| | $H_2O_2$ concentration | | | |
|---|---|---|---|---|
| | 0.25 mM | | 2.5 mM | |
| Dye No. | PSP | VAN | PSP | VAN |
| 1 | 0.04 | — | 0.13 | 0.07 |
| 2 | >5 | >5 | — | — |
| 3 | 0.37 | 0.18 | — | — |
| 4 | — | — | 0.15 | 0.12 |
| 5 | — | — | 0.06 | 0.03 |
| 6 | — | — | 0.05 | 0.04 |
| 7 | >5 | >5 | — | — |
| 8 | 0.11 | 0.13 | 0.14 | 0.12 |

A bleaching effect on the dye solution was seen in all cases, although large variations are seen among the different dyes. In most cases, PSP was superior to VAN as accelerator.

EXAMPLE 3

Backstaining Inhibition

As indicated below, different fabrics printed with different reactive dyes and different thickeners were tested. In each experiment the printed fabric was rinsed cold in a washing machine and then washed for 30 minutes with the following wash liquor:

1 g/l of nonionic surfactant (Sandopan ™ LFW)
0.2M phosphate +0.1M citric acid, pH 6.5
5 PODU/g of peroxidase from Coprinus
5 μM of accelerator (PSP or VAN)
0.25M $H_2O_2$ The optical density (OD) of the spent washing liquor was measured at 570 nm for blue dye and 667 nm for turquoise dye. Reference experiments without peroxidase, accelerator and hydrogen peroxide were included for comparison. The experimental conditions and results are shown in the table below. In experiments 1–6, the washing was performed in sealed glass beakers with back-and-forth motion (135 motions per minute; 0.4 g of fabric and 20 g of wash liquor was used in each beaker (i.e. liquor ratio 1:50). In experiments 7–10, the washing was done in a Launderometer laboratory washing machine, using 5 g of fabric and 100 g of wash liquor in each steel beaker (liquor ratio 1:20).

| Experiment | 1 | 2 | 3 | 4 | 5 | 6 | 7 | 8 | 9 | 10 |
|---|---|---|---|---|---|---|---|---|---|---|
| Fabric | Woven viscose | | Woven viscose | | Knitted cotton | | Woven viscose | | Woven viscose | |
| Dye | Turquoise | | Turquoise | | Blue | | Turquoise | | Turquoise | |
| Thickener | Galactomannan | | British gum | | Alginate | | Alginate | | Galactomannan | |
| Wash temp. | 40° C. | | 40° C. | | 40° C. | | 40 | 60 | 40° C. | |
| Wash pH | 6.5 | | 6.5 | | 6.5 | | 6.5 | 6.5 | 5.0 | 7.0 |
| OD of reference | 0.583 | | 0.708 | | 0.584 | | 0.510 | 0.912 | 1.129 | 0.745 |
| Accelerator | VAN | PSP | VAN | PSP | VAN | PSP | PSP | | PSP | |
| Wash liquor OD | 0.107 | 0.093 | 0.093 | 0.074 | 0.246 | 0.225 | 0.151 | 0.350 | 0.037 | 0.153 |

The above results show a significant decrease of the colour of the spent wash liquor in each case.

The textile used in experiments 9–10 was printed in stripes. The remission of the white parts was measured at 580 nm; improved whiteness (higher remission) was seen compared to the reference.

Similar experiments were made using 10 times higher concentration of peroxidase, $H_2O_2$, and accelerator. Decolourization of the wash liquor was observed in all cases, but less than the experiments with the lower concentration.

EXAMPLE 4

Treatment of Dyed Fabric

Knitted, bleached 100% cotton fabric was dyed in a Jet-dyer at the following conditions:

Water: 20 l/kg fabric
Dye: Primazin Brilliant Blue RL, 0.5% of fabric weight
NaCl: 100% of fabric weight
$Na_2CO_3$: 10% of fabric weight
NaOH: 1% of fabric weight The dyeing operated started at pH 7 and 40° C., increasing to 80° C. (1° C./min) and holding at 80° C. for 60 minutes. NaCl was added 15 minutes after start, and $Na_2CO_3$ and NaOH 40 minutes after start.

The fabric was centrifuged and cut into test pieces of 0.8 g wet weight, 0.4 g dry weight each. These were treated as follows:

Cold rinse
30 min wash at 50° C. using
   1 g/l nonionic surfactant (Sandopan LFW)
   5 PODU/g peroxidase from Coprinus
   50 μM accelerator (VAN or PSP)
   2.5 mM $H_2O_2$
   pH 6.5
Cold rinse
30 min wash at 90° C. using
   1 g/l anionic/nonionic detergent (Tanaterge RE)
Cold rinse
Drying The optical density was measured at 595 nm in the wash liquor after each wash. A reference experiment was made at the same conditions, but without peroxidase, accelerator and $H_2O_2$. The results were as follows:

| Accelerator | OD after 1st wash | OD after 2nd wash |
| --- | --- | --- |
| None (reference) | 0.213 | 0.071 |
| VAN | 0.078 | 0.038 |
| PSP | 0.062 | 0.036 |

It is seen that use of an enzymatic bleaching system according to the invention in the first washing step significantly decreases the colour of the spent wash liquor after this washing step and also after the subsequent non-enzymatic washing step.

We claim:

1. A process for removing excess dye from a newly manufactured printed or dyed fabric or yarn, comprising treating said fabric or yarn with a wash liquor containing (a) an enzyme exhibiting peroxidase activity and a suitable source of $H_2O_2$ or (b) an enzyme exhibiting a suitable oxidase activity and a source of $O_2$.

2. The process according to claim 1, wherein the enzyme is a catechol oxidase, a laccase, a peroxidase or a chloride peroxidase.

3. The process according to claim 2, wherein the enzyme is a peroxidase derived from a strain of Coprinus or *B. pumilus*.

4. The process according to claim 1, wherein the enzyme is used in an amount of 1-100 mg of enzyme protein per 1 of the wash liquor.

5. The process according to claim 1, wherein the source of $H_2O_2$ is hydrogen peroxide, a perborate or a percarbonate.

6. The process according to claim 5, wherein the source of $H_2O_2$ is present in an amount corresponding to 0.1-5 mM $H_2O_2$.

7. The process according to claim 1, wherein the source of $H_2O_2$ is an enzymatic system capable of generating hydrogen peroxide.

8. The process according to claim 1, wherein the wash liquor further comprises an additional oxidizable substrate selected from the group consisting of a metal ion, a halide ion and an organic compound.

9. The process according to claim 8, wherein the organic compound is a phenol.

10. The process according to claim 9, wherein the organic compound is p-hydroxycinnamic acid or 2,5-dichlrophenol.

11. The process according to claim 8, wherein the oxidizable substrate is present in an amount between about μM and about 1 mM.

12. The process according to claim 1, wherein the wash liquor further comprises a cellulase and/or pumice 13. The process according to claim 1, wherein the wash liquor further comprises an α-amylase.

14. A process for simultaneously removing excess dye from and forming localized color variation on a fabric, comprising treating said fabric or yarn with a wash liquor containing (a) an enzyme exhibiting peroxidase activity and a suitable source of $H_2O_2$ or (b) an enzyme exhibiting a suitable oxidase activity and a source of $O_2$, wherein the wash liquor further contains a cellulase and/or pumice.

15. A process for simultaneously removing excess dye and starch size from a fabric, comprising treating said fabric or yarn with a wash liquor containing (a) an enzyme exhibiting peroxidase activity and a suitable source of $H_2O_2$ or (b) an enzyme exhibiting a suitable oxidase activity and a source of $O_2$, wherein the wash liquor further contains an α-amylase.

* * * * *